United States Patent
Kasevich

[19]
[11] Patent Number: 6,016,452
[45] Date of Patent: Jan. 18, 2000

[54] DYNAMIC HEATING METHOD AND RADIO FREQUENCY THERMAL TREATMENT

[76] Inventor: Raymond S. Kasevich, 55 Pepperell Way, York, Me. 03909

[21] Appl. No.: 08/820,111

[22] Filed: Mar. 19, 1997

Related U.S. Application Data

[60] Provisional application No. 60/013,659, Mar. 19, 1996.

[51] Int. Cl.⁷ .......................................... A61F 2/00
[52] U.S. Cl. .............................. 607/101; 606/41; 606/49; 606/50
[58] Field of Search ............................. 607/98–102, 113, 607/116, 154, 128; 606/27–28, 32–34, 41, 48, 50

[56] References Cited

U.S. PATENT DOCUMENTS

| | | |
|---|---|---|
| Re. 32,057 | 12/1985 | LeVeen . |
| Re. 32,066 | 1/1986 | LeVeen . |
| 3,991,770 | 11/1976 | LeVeen . |
| 4,011,872 | 3/1977 | Komiya . |
| 4,121,592 | 10/1978 | Whalley . |
| 4,154,246 | 5/1979 | LeVeen . |
| 4,237,898 | 12/1980 | Whalley . |
| 4,280,503 | 7/1981 | Ackerman . |
| 4,311,154 | 1/1982 | Sterzer et al. . |
| 4,411,266 | 10/1983 | Cosman . |
| 4,423,727 | 1/1984 | Widran et al. . |
| 4,448,198 | 5/1984 | Turner . |
| 4,503,855 | 3/1985 | Maslanka . |
| 4,565,200 | 1/1986 | Cosman . |
| 4,601,296 | 7/1986 | Yerushalmi . |
| 4,658,836 | 4/1987 | Turner . |
| 4,676,258 | 6/1987 | Inokuchi et al. . |
| 4,763,671 | 8/1988 | Goffinet . |
| 4,798,215 | 1/1989 | Turner ...................................... 607/102 |
| 4,805,616 | 2/1989 | Pao . |
| 4,823,791 | 4/1989 | D'Amelio et al. . |
| 4,896,671 | 1/1990 | Cunningham et al. . |
| 4,907,589 | 3/1990 | Cosman . |
| 4,917,082 | 4/1990 | Gross et al. . |
| 4,920,978 | 5/1990 | Covin . |
| 4,950,267 | 8/1990 | Ishihara et al. . |
| 4,955,377 | 9/1990 | Lennox et al. . |
| 4,966,597 | 10/1990 | Cosman . |
| 4,979,948 | 12/1990 | Geddes et al. . |
| 5,007,908 | 4/1991 | Rydell . |

(List continued on next page.)

FOREIGN PATENT DOCUMENTS

| | | |
|---|---|---|
| 0608609 | 8/1994 | European Pat. Off. . |
| 2119253 | 11/1983 | United Kingdom . |
| 2121675 | 5/1990 | WIPO . |
| 9004365 | 5/1990 | WIPO . |
| 9103996 | 4/1991 | WIPO . |
| 9116859 | 11/1991 | WIPO . |
| 9210142 | 6/1992 | WIPO . |
| 9220290 | 11/1992 | WIPO . |
| 9304727 | 3/1993 | WIPO . |
| 9315664 | 8/1993 | WIPO . |
| WO9513027 | 5/1995 | WIPO . |
| WO9706857 | 2/1997 | WIPO . |

OTHER PUBLICATIONS

Radionics® Neurosurgical Instruments, 1981 Radionics, Inc.

*Primary Examiner*—John P. Lacyk
*Assistant Examiner*—Ryan Carter

[57] ABSTRACT

A method and system for the delivery of radiofrequency energy to the tissue, particularly, the prostate, to alleviate the symptoms of BPH is disclosed. The system incorporates a bipolar or multipolar electrode array to create an electric field where the heat created is confined solely to a specific volume of the prostate gland and therefore the heated tissue is defined only by the electrode geometry. The bipolar electrode array provides a variety of three dimensional, symmetric heating patterns within the prostatic tissue depending on the relative electrode lengths and angular separation. The system provides precision tissue temperature and impedance measurements thereby enabling the surgeon to accurately predict heating pattern performance and tissue response to RF heating.

21 Claims, 15 Drawing Sheets

U.S. PATENT DOCUMENTS

| | | |
|---|---|---|
| 5,057,107 | 10/1991 | Parins et al. . |
| 5,078,716 | 1/1992 | Doll . |
| 5,083,565 | 1/1992 | Parins . |
| 5,084,044 | 1/1992 | Quint . |
| 5,098,431 | 3/1992 | Rydell . |
| 5,151,100 | 9/1992 | Abele et al. . |
| 5,159,925 | 11/1992 | Neuwirth et al. . |
| 5,186,181 | 2/1993 | Franconi et al. . |
| 5,191,883 | 3/1993 | Lennox et al. . |
| 5,192,280 | 3/1993 | Parins . |
| 5,197,963 | 3/1993 | Parins . |
| 5,220,927 | 6/1993 | Astrahan et al. . |
| 5,246,438 | 9/1993 | Langberg . |
| 5,249,585 | 10/1993 | Turner et al. . |
| 5,273,524 | 12/1993 | Fox et al. . |
| 5,282,799 | 2/1994 | Rydell . |
| 5,290,286 | 3/1994 | Parins . |
| 5,295,955 | 3/1994 | Rosen et al. . |
| 5,300,068 | 4/1994 | Rosar et al. . |
| 5,301,687 | 4/1994 | Wong et al. . |
| 5,304,214 | 4/1994 | DeFord et al. . |
| 5,318,563 | 6/1994 | Malis et al. . |
| 5,330,518 | 7/1994 | Neilson et al. . |
| 5,334,193 | 8/1994 | Nardella . |
| 5,341,807 | 8/1994 | Nardella . |
| 5,342,357 | 8/1994 | Nardella . |
| 5,364,392 | 11/1994 | Warner et al. . |
| 5,368,591 | 11/1994 | Lennox et al. . |
| 5,370,675 | 12/1994 | Edwards et al. . |
| 5,383,876 | 1/1995 | Nardella . |
| 5,383,917 | 1/1995 | Desai et al. . |
| 5,385,544 | 1/1995 | Edwards et al. . |
| 5,401,274 | 3/1995 | Ksunoki . |
| 5,403,311 | 4/1995 | Abele et al. . |
| 5,409,006 | 4/1995 | Buchholtz et al. . |
| 5,409,453 | 4/1995 | Lundquist et al. . |
| 5,413,588 | 5/1995 | Rudie et al. . |
| 5,421,819 | 6/1995 | Edwards et al. . |
| 5,423,808 | 6/1995 | Edwards et al. . |
| 5,431,649 | 7/1995 | Mulier et al. . |
| 5,435,805 | 7/1995 | Edwards et al. . |
| 5,437,662 | 8/1995 | Nardella . |
| 5,441,498 | 8/1995 | Perkins . |
| 5,454,782 | 10/1995 | Perkins . |
| 5,458,597 | 10/1995 | Edwards et al. . |
| 5,464,437 | 11/1995 | Reid et al. . |
| 5,464,445 | 11/1995 | Rudie et al. . |
| 5,470,308 | 11/1995 | Edwards et al. . |
| 5,470,309 | 11/1995 | Edwards et al. . |
| 5,472,441 | 12/1995 | Edwards et al. . |
| 5,484,400 | 1/1996 | Edwards et al. . |
| 5,486,161 | 1/1996 | Lax et al. . |
| 5,507,743 | 4/1996 | Edwards et al. . |
| 5,509,929 | 4/1996 | Hascoet et al. . |
| 5,514,130 | 5/1996 | Baker . |
| 5,531,676 | 7/1996 | Edwards et al. . |
| 5,531,677 | 7/1996 | Lundquist et al. . |
| 5,536,240 | 7/1996 | Edwards et al. . |
| 5,540,655 | 7/1996 | Edwards et al. . |
| 5,540,681 | 7/1996 | Strul et al. . |
| 5,542,915 | 8/1996 | Edwards et al. . |
| 5,542,916 | 8/1996 | Hirsch et al. . |
| 5,545,161 | 8/1996 | Imran . |
| 5,599,294 | 2/1997 | Edwards et al. . |
| 5,599,345 | 2/1997 | Edwards et al. . |
| 5,599,346 | 2/1997 | Edwards et al. . |
| 5,827,276 | 10/1998 | LeVeen et al. .................. 606/41 |

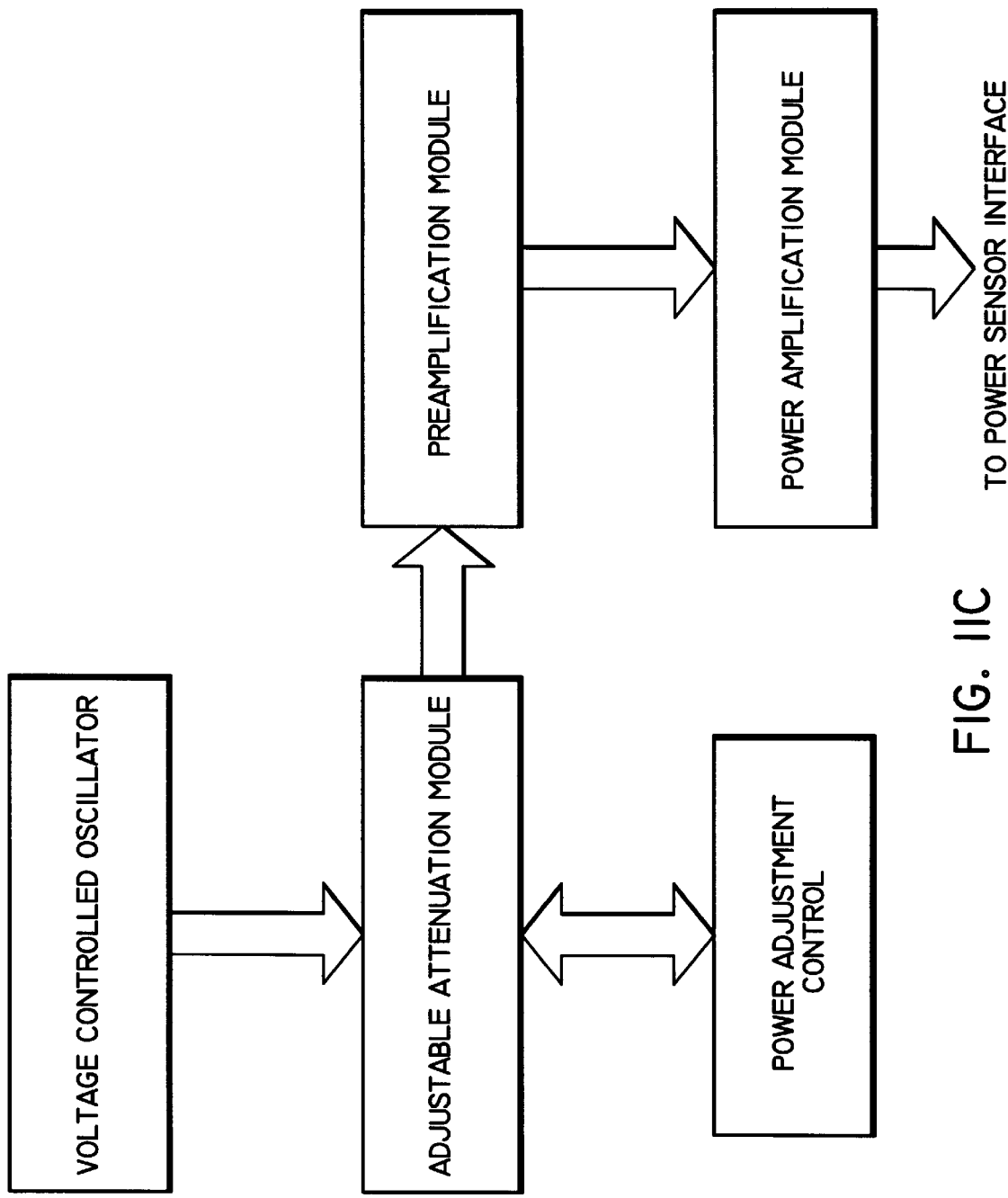
FIG. IIC

DYNAMIC HEATING METHOD AND RADIO FREQUENCY THERMAL TREATMENT

CROSS REFERENCE TO RELATED APPLICATION(S)

This application claims priority from provisional application No. 60/013,659, filed Mar. 19, 1996.

BACKGROUND

1. Technical Field

The present disclosure relates generally to a method and system for thermal treatment of tissue, and, more particularly, to a method and system for the hyperthermia treatment of prostatic tissue.

2. Description of Related Art

Benign prostate hyperplasia (BPH) or hyperplasia affects over one out of every two males over the age of fifty. BPH is the non-cancerous enlargement of the prostate gland and is characterized generally by a constriction of the urethra by the prostate gland. An array of symptoms are associated with BPH including frequent urination, complications in urinary flow and associated pain.

Generally there are two primary methods for treating BPH, namely, drug therapy and surgical intervention. Drug therapy incorporates the use of one or more drugs such as Proscar™ and Hydrin™ to either reduce the size of the prostate or to relax the urethral muscles thereby facilitating the normal functioning of the urinary system. Known drug therapies, however, are limited in their effectiveness and present many drug side effect concerns.

Surgical methods for treating BPH include transurethral resection of the prostate (TURP), transurethral incision of the prostate (TUIP), visual laser assisted prostatectomy (VLAP), balloon dilation and stenting. TURP is the most common method employed for BPH treatment today and involves the insertion of an electrosurgical cutting instrument through the urethral passage. The cutting elements of the instrument are positioned adjacent the prostate gland, and the instrument is energized such that the cutting elements selectively cauterize and resect tissue from the core of the prostate. The TURP procedure, however, has many side effects including bleeding, electrograde ejaculation, impotence, incontinence, edema and a prolonged recovery period for the patient. An example of an electrosurgical cutting instrument utilized in conjunction with a TURP procedure is disclosed in U.S. Pat. No. 5,192,280.

Transurethral incision of the prostate (TUIP) involves the use of an electrocautery device which is passed through the urethra. The device is employed to make multiple incisions in the prostate, thereby permitting the prostate to be displaced from the urethra wall to create an opening for urine flow. Success with the TUIP procedure is generally limited providing only temporary relief and requiring a subsequent repeat of the procedure in the future.

Visual laser assisted prostatectomy (VLAP) includes insertion of a laser catheter through the urethra and directing laser energy laterally through the catheter sleeve at the urethral wall and the prostatic tissue. The laser energy causes the tissue to coagulate. The coagulated tissue eventually necrosis from lack of blood flow and is naturally removed from the body. Drawbacks of VLAP include increased recovery time, acute pain and irritation, and undesired burning of the urethral wall. Examples of methods and apparatuses utilized in VLAP treatment of BPH are disclosed in U.S. Pat. No. 5,242,438 to Saadatmanesh et al. and U.S. Pat. No. 5,322,507 to Costello.

Balloon dilation procedures for BPH involve expanding and stretching the enlarged prostate with a balloon catheter to relieve pressure off the constricted urethra while stenting incorporates the insertion of tiny wire-mesh coils which expand into a scaffold to hold the urethra open. Balloon dilation and stenting, however, are only temporary procedures typically requiring follow up within a year period. In addition, stenting presents complications of stent migration and consequent irritation.

More recently, two new surgical developments, namely, transurethral microwave therapy (TUMT) and high intensity focused ultrasound (HIFU) have been developed for the treatment of BPH. In accordance with a TUMT procedure, a foley-type urethral catheter having a microwave emitting antenna at a probe end is inserted into the urethral passage for a period of time sufficient to treat the tissue by microwave radiation. Intraurethral applicators of this type are described in U.S. Pat. Nos. 4,967,765, 5,234,004 and 5,326,343. The drawbacks of TUMT include the inability to focus the heat energy in the prostatic area and the inability to achieve high temperatures uniformly within the prostate.

High intensity focused ultrasound (HIFU) includes directing high intensity ultrasound waves at the prostate tissue to create heat in a precise area to coagulate and necrose tissue. A transurethral probe is utilized to create the ultrasound beams for both imaging and ablation of the prostatic tissue. Disadvantages of this procedure include the inability to directly focus the ultrasound energy at the prostatic tissue.

A more recent form of treatment for BPH involves thermally treating prostatic tissue with radio frequency electromagnetic energy. For example, one current technique, known as transurethral needle ablation TUNA™), involves the transurethral application of a medical probe having a pair of monopolar RF needle electrodes at its distal end. The probe is inserted into the urethra and advanced to a position adjacent the prostate. Thereafter, the RF needles are advanced to penetrate the urethral wall and access the prostatic tissue. A RF current is transmitted through each electrode and passes through the tissue to a grounding pad to form a necrotic legion which is eventually absorbed by the body. Apparatuses and methods for treating BPH via the TUNA™ technique are disclosed for example in U.S. Pat. Nos. 5,366,490; 5,370,675; 5,385,544; 5,409,453; and 5,421,819.

The use of RF electromagnetic energy in the thermal treatment of BPH such as in, e.g., the aforedescribed TUNA™ technique, has several limitations. In particular, the use of monopolar RF electrodes presents problems in localizing thermal energy within a desired heating pattern within the prostatic tissue. Moreover, the heating patterns generated by the TUNA procedure with the monopolar electrode arrangement are nonsymmetrical. In addition, the leakage of RF current from the monopolar electrodes to the grounding pad increases the potential of healthy tissue being subjected to thermal energy and destroyed. Furthermore, the monopolar electrode arrangement of the TUNA instrument is limited with respect to its ability to generate heating patterns of various dimensions. Also, monopolar systems require higher frequency applications.

Another significant disadvantage associated with the TUNA™ technique concerns the impedance measurements generated with the monopolar electrode and grounding pad arrangement. The electrical impedance of an RF electrode system of a thermal treatment instrument is generally determined during treatment to ascertain the dielectric properties of the treated tissue to thereby provide an indication of the state of the treated tissue and its response to the RF heating pattern. However, with a monopolar electrode system, such as the system utilized in the TUNA™ technique, the impedance is dependent upon, in part, the location of the grounding pad relative to the electrode. Thus, a direct measure of the prostatic tissue impedance cannot be ascertained.

Another disadvantages of current RF thermal treatment systems is that these systems are capable of only achieving necrosis of the treated tissue as opposed to complete vaporization. Necrotic tissue entails a two to four week period for complete absorption and natural removal from the body thereby delaying immediate relief of the symptoms of BPH.

SUMMARY

Accordingly, the present disclosure is directed to a method and system for the delivery of radiofrequency energy to the tissue, particularly, the prostate, to alleviate the symptoms of BPH. The system incorporates a bipolar or multipolar electrode array to create an electric field where the heat created is confined solely to a specific volume of the prostate gland and therefore the heated tissue is defined only by the electrode geometry. The bipolar electrode array provides a variety of three dimensional, symmetric heating patterns within the prostatic tissue depending on the relative electrode lengths and angular separation. The system provides precision tissue temperature and impedance measurements thereby enabling the surgeon to accurately predict heating pattern performance and tissue response to RF heating.

In a preferred embodiment, the apparatus includes a handle assembly, and an elongate body extending distally from the handle assembly and having an axial bore extending at least partially therethrough defining a longitudinal axis. First, second, and third elongated probes are supported within the elongate body and are mounted for movement between respective retracted positions disposed within the axial bore and respective deployed positions projecting outwardly from a distal end portion of the elongate body. A first actuator is associated with the handle assembly and is operatively connected to the first probe for moving the first probe between retracted and deployed positions independent of the second and third probes. A second actuator is associated with the handle assembly and is operatively connected to the second and third probes for conjunctively moving the second and third probes between retracted and deployed positions independent of the first probe. A coupling extends from a proximal end of the handle assembly for operatively connecting the first, second, and third probes to an external source of radiofrequency energy.

Preferably, first, second and third guide channels are defined in a distal end portion of the elongated body in communication with the axial bore thereof for respectively directing the first second and third probes outwardly toward the respective deployed positions thereof.

Preferably, the first, second and third probes are each configured as a bipolar electrode, and each is provided with insulation. However, a distal portion of each probe is without insulation so as to define first, second and third energy radiating segments. Upon deployment of the first, second and third probes, the first, second and third radiating segments are oriented within the same geometric plane and form a selected three dimensional heating pattern.

The transmission line electrode array (TLEA) system of the present disclosure is intended to deliver electromagnetic energy to tissue for thermal treatment of the tissue including tissue ablation, tissue vaporization and/or tissue coagulation. The TLEA system has particular application in the treatment of benign prostate hyperplasia (BPH) with electromagnetic radio frequency (RF) energy, however, it is to be appreciated that the TLEA system is not limited to such application. For example, the TLEA system is not necessarily limited to the treatment of BPH but may be used in other surgical procedures such as cardiac ablation, cancer treatment, etc. . . Moreover, TLEA system may be used in any minimally invasive surgical procedure (e.g., endoscopic, laparoscopic, etc..) where thermal treatment of tissue is desired and access to the tissue is limited.

BRIEF DESCRIPTION OF THE PREFERRED EMBODIMENT(S)

Various embodiments of the present disclosure are described herein with reference to the drawings, wherein:

FIG. 11C is a block diagram illustrating the components of the power generator/power amplifier subsystem;

DETAILED DESCRIPTION OF THE PREFERRED EMBODIMENTS

Overview

Figure 1:
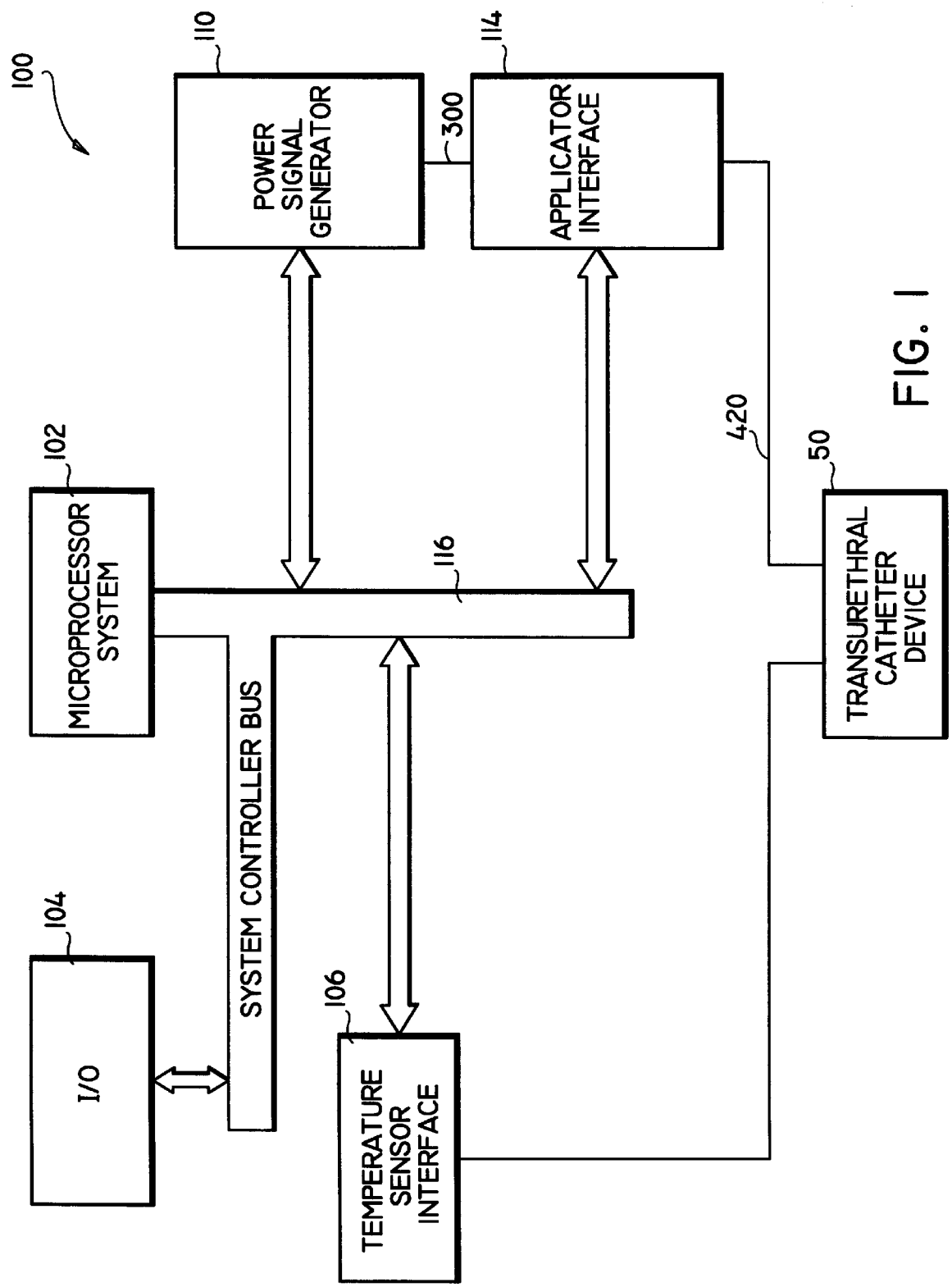
FIG. 1 is a block diagram illustrating the transmission line electrode array system (TLEA) in accordance with the principles of the present disclosure.

In FIG. 1, there is illustrated a block diagram of the transmission line electrode array (TLEA) system configured in accordance with the principles of the present disclosure. As shown, system 10 generally includes transurethral applicator 50 and control system 100. Control system 100 supports the various functions of applicator 50 and will be discussed in greater detail hereinbelow. Applicator 50 is a catheter-type instrument appropriately dimensioned for insertion within the urethral passage of a patient. The applicator 50 preferably selectively deploys three bipolar radio frequency (RF) electrodes, within the targeted tissue and is capable of generating a variety of three dimensional, symmetric heating patterns within the tissue.

Transurethral Applicator

Figure 2:
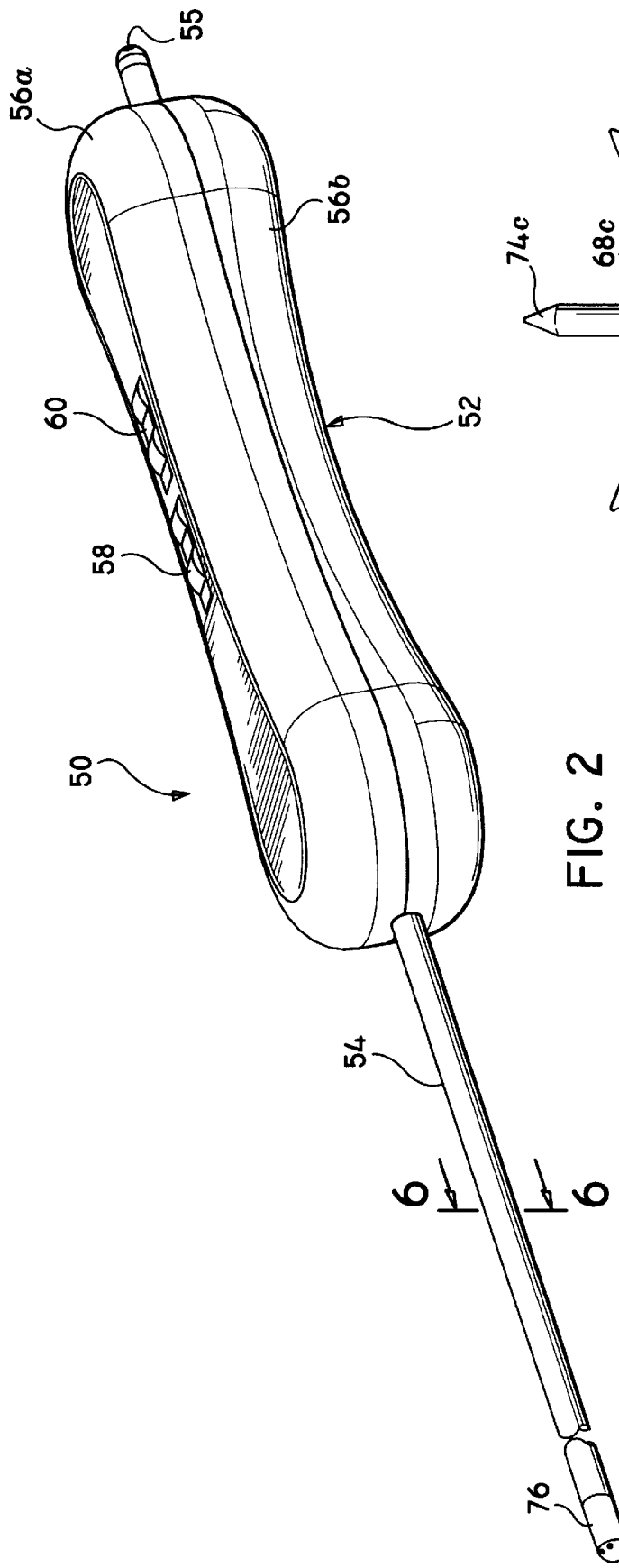
FIG. 2 is a perspective view of the transurethral applicator of the TLEA system of FIG. 1 illustrating the housing and the elongated body portion thereof.
Figure 3:
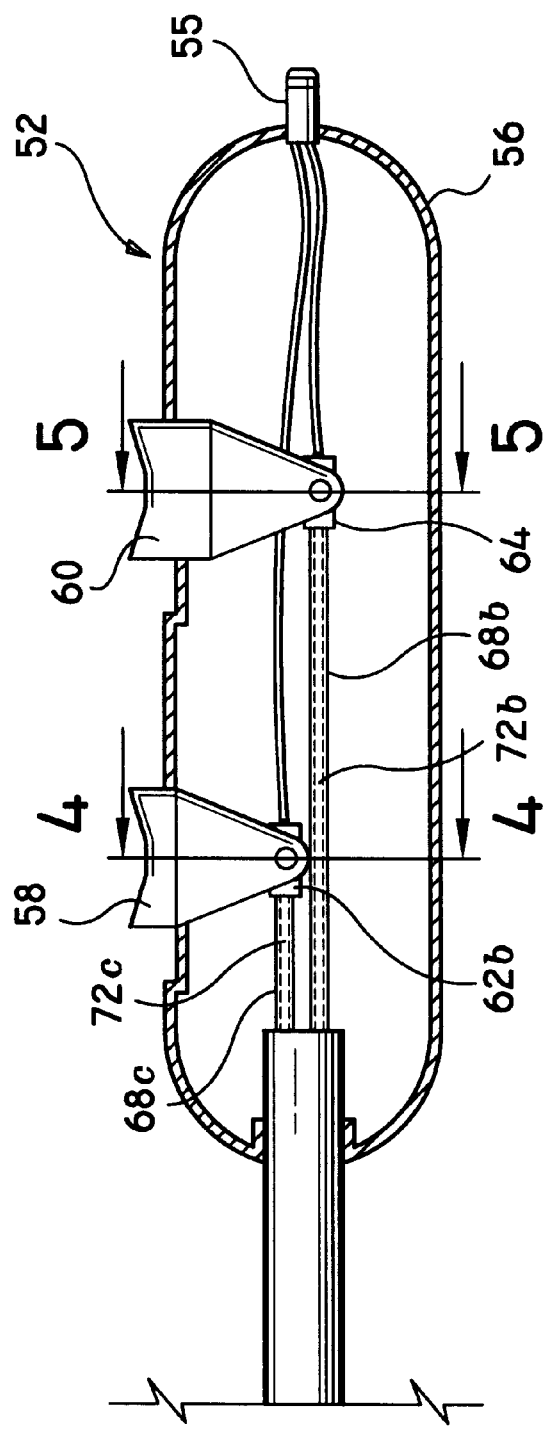
FIG. 3 is a cross-sectional view of the housing of the applicator illustrated in FIG. 2.

Referring now to FIGS. 2–3, transurethral applicator 50 includes housing 52 which defines a handle and an elongated body portion 54 connected to the housing 52 and extending distally therefrom. Housing 52 preferably consists of two half sections 56a and 56b connected to each other along their peripheries by suitable means such as, for example, fasteners or adhesives. Half sections 56a and 56b may be fabricated from a suitable polymeric material, or in the alternative, an aluminum or steel alloy. Housing 52 is advantageously configured to be grasped with a single hand and is ergonomically contoured for user comfort. Preferably, an electrical coupling 55 extends from a proximal end of housing 52 for receiving a cable 57 which connects applicator 50 and control system 100 (see generally FIG. 14).

Figure 5:
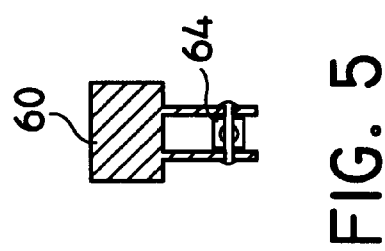
FIG. 5 is a cross-sectional view taken along the lines 5—5 of FIG. 3 illustrating the connection of the second actuating member to the second drive member which deploys the centrally located radio frequency bipolar electrode.
Figure 4:
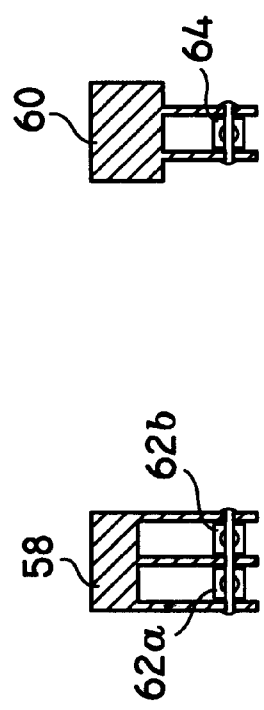
FIG. 4 is a cross-sectional view taken along the lines 4—4 of FIG. 3 illustrating the connection of the first actuating member to the first drive member which simultaneously deploys a pair of radio frequency bipolar electrodes.

Referring now to FIGS. 3–5, in conjunction with FIG. 2, housing 52 includes first and second slidable actuating members 58 and 60. Actuating member 58 is operatively connected to parallel drive members 62a and 62b. Actuating member 60 is operatively connected to single drive member 64. Actuating members 58 and 60 are mounted for reciprocal longitudinal movement relative to housing 52 to selectively move a plurality of electrodes between nondeployed and fully deployed positions as will be discussed hereinbelow.

Figure 6:
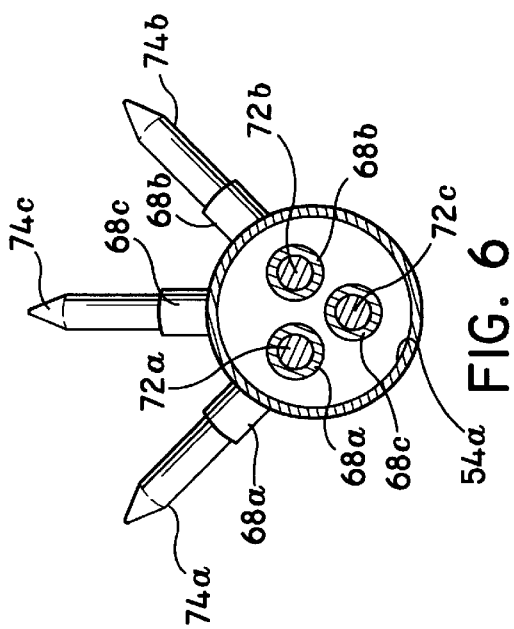
FIG. 6 is a cross-sectional view taken along the lines 6—6 of FIG. 2 illustrating the electrodes within the elongated portion.
Figure 7:
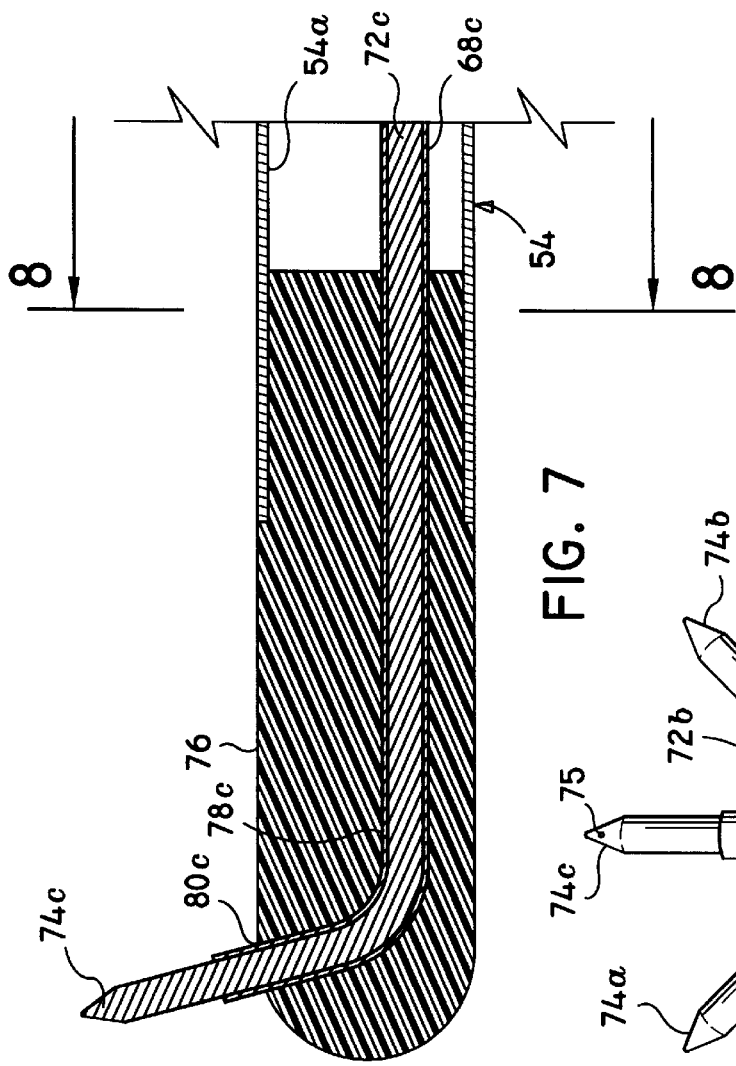
FIG. 7 is a side cross-sectional view of the deployment tip of the transurethral applicator illustrating deployment of the bipolar electrodes from the deployment tip.
Figure 8:
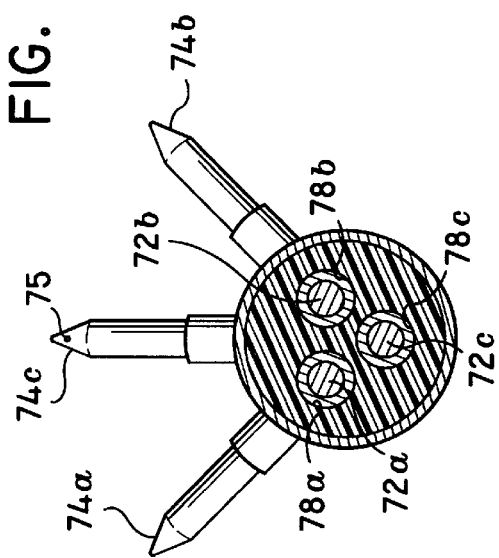
FIG. 8 is a cross-sectional view taken along the lines 8—8 of FIG. 7 illustrating the deployment channels in the deployment tip for deploying the electrodes.

Referring now to FIGS. 6–8, in conjunction with FIG. 2, the elongated body portion 54 of apparatus 50 defines an axial bore 54a having a longitudinal axis extending therethrough. Three bipolar electrodes 72a–72c are mounted for reciprocal longitudinal movement within body portion 54 in response to selective manipulation of actuating members 58 and 60.

Bipolar electrodes 72a–72c are each preferably formed of a thin solid wire capable of carrying an electromagnetic radio frequency (RF) current. The electrodes each have a pointed tip 74a–74c to facilitate penetration through body tissue. Each electrode is insulated along a major portion of its length to prevent damage to non-targeted body tissue. More specifically, the insulation designated by reference numerals 68a–68c cover the entire length of each electrode except for the distal end portions thereof which are exposed to transmit the electromagnetic RF current to the targeted body tissue. Alternatively, a resistive coating can be utilized along the entire length of the probe which can create currents which are constant to provide uniform heating.

At least one of the electrodes (preferably electrode 72c) includes a temperature sensing element 75. The temperature sensing element can consist of conventional hardwire thermometry such as a thermistor, for example. Preferably, however, to avoid electromagnetic interference between the electrodes, temperature sensing element 75 consists of a fiber optic temperature sensor. Alternatively, a hollow cable with a thermocouple positioned therein can also be utilized. This allows a smaller diameter cable to be used. Further details of the electrodes will be provided hereinbelow.

With reference to FIG. 3, the two bipolar electrodes 72a and 72b are operatively connected to drive members 62a–62b, respectively. Bipolar electrode 72c is operatively connected to drive member 62c. Accordingly, longitudinal movement of actuating member 58 causes corresponding conjunctive movement of electrodes 72a and 72b and longitudinal movement of actuating member 60 causes corresponding movement of electrode 72c. Thus, the user can selectively deploy the three electrodes 72a–72c to predetermined geometries to produce different effective heating patterns as will be discussed hereinbelow. Preferably, as best seen in FIG. 3, conductive wires connect each of the three probes to coupling 55 to deliver the radiofrequency energy therebetween. The particular method utilized to connect the probes/electrodes to their respective drive rods may be readily determined by one skilled in the art.

Referring now to FIGS. 7–10, a deployment tip 76 is mounted to the distal end of body portion 54. Deployment tip 76 includes three electrode deployment channels 78a–78c formed therein which extend radially outwardly from the axis of the body portion. Each deployment channel includes a deployment port 80a–80c which is defined in the outer peripheral surface of deployment tip 76. Deployment channels 78a–78c respectively guide electrodes 72a–72c from the axial bore 54a of body portion 54 into the targeted body tissue in a desired formation.

Figure 10:
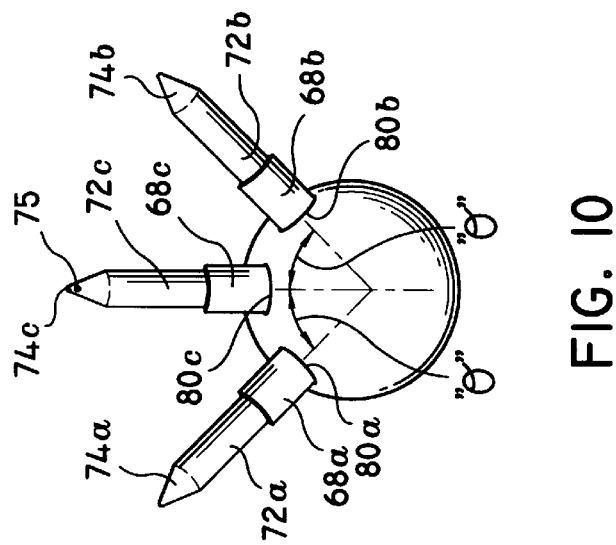
FIG. 10 is an axial view of the elongated portion illustrating deployment of the RF bipolar electrodes from the elongated portion.
Figure 9:
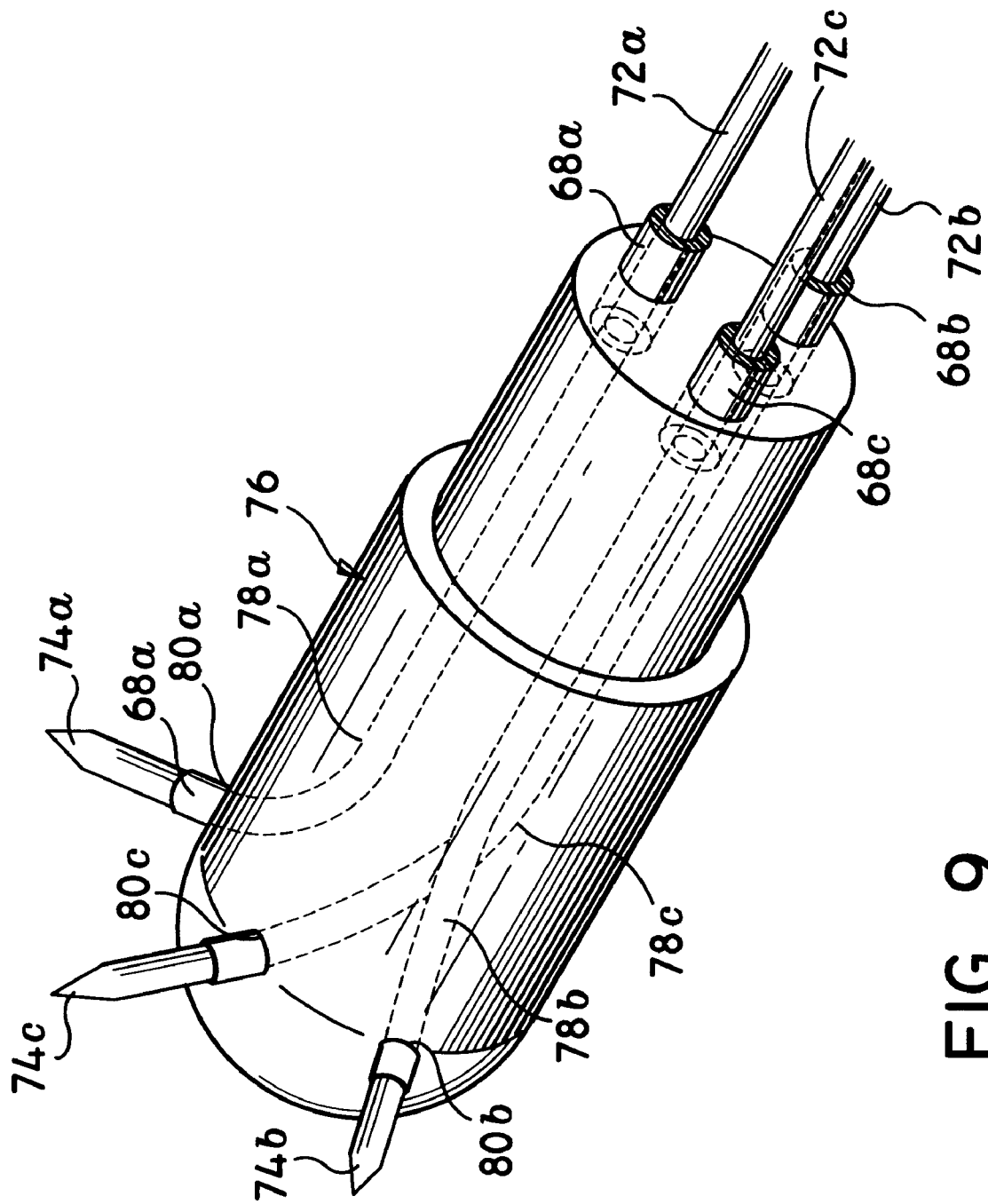
FIG. 9 is a perspective view of the deployment tip further illustrating the deployment channels.

As depicted in FIGS. 9–10, the central deployment port 80c is disposed equidistant from the two radially outermost deployment ports 80a and 80b. Deployment ports 80a and 80b are preferably arranged such that the deployed energy radiating portions of electrodes 72a and 72b are oriented at the same angle "O" (FIG. 10) relative to the central deployed electrode 72c. Preferably, the deployed energy radiating portions or tips of the electrode portions of each of the electrodes lie within the same geometric plane. In this manner, the deployed electrodes generate a uniform symmetrical thermal pattern for heating body tissue. Preferred arrangements of the deployed electrodes will be discussed in greater detail hereinbelow.

Control Unit

Referring again to the block diagram of FIG. 1, the control unit of the TLEA system will be discussed. As shown, control unit 100 includes microprocessor system 102 which functions as a system controller, for inputting commands and outputting information via input/output (I/O) or display device 104. Microprocessor system (controller) 102 also initiates and controls temperature sensor interface 106, power signal generator 110, and applicator interface 114, via system bus 116. Microprocessor system 102 may be any of a variety of microprocessor systems available. An exemplary microprocessor system includes a 486 DX4/100 central processing unit (CPU). As is well known in the art, such microprocessor systems may also include Random Access Memory (RAM), Read Only Memory (ROM) and Input/Output (I/O) capabilities. Microprocessor system 102 can use a program called "LAB VIEW", developed by National Instruments, for example, that allows system 102 to perform as a virtual instrument. Temperature sensor interface 106 receives signals from transurethral applicator 50 processes the signals and provides real time temperature information to microprocessor system 102. This allows microprocessor system 102 to monitor the temperature of the tissue in the area being treated.

Figure 1A:
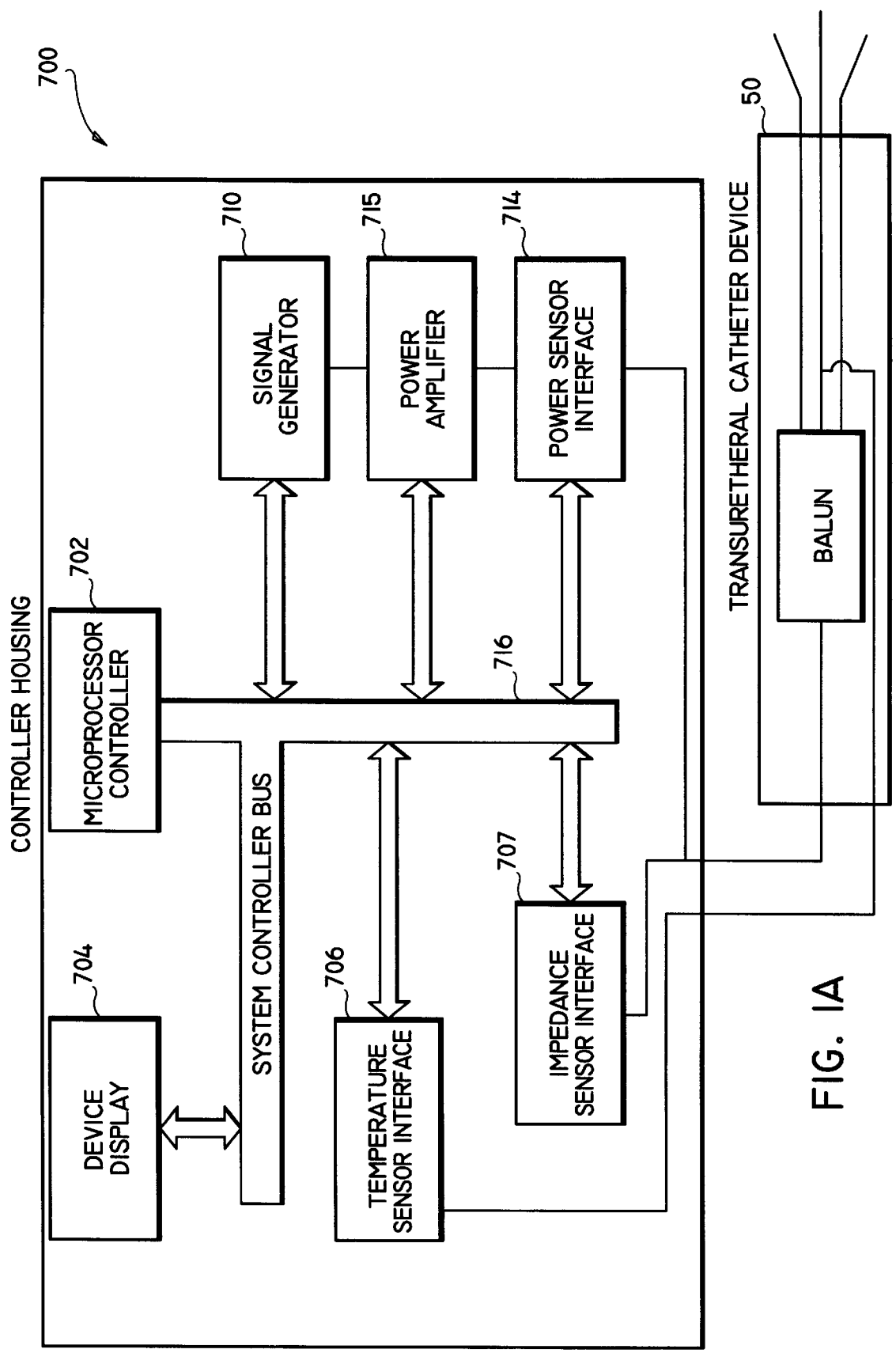
FIG. 1A is a block diagram illustrating an alternate embodiment of the control unit of the transmission line electrode array system.

FIG. 1A illustrates an alternate embodiment of the control unit of the TLEA system. Control unit 700 includes microprocessor controller 702 and device display 704. Microprocessor controller 702 initiates and controls temperature sensor interface 706, impedance sensor interface 707, power signal generator 710, power amplifier 715 and power sensor interface 714 via system bus 716.

Figure 11B:
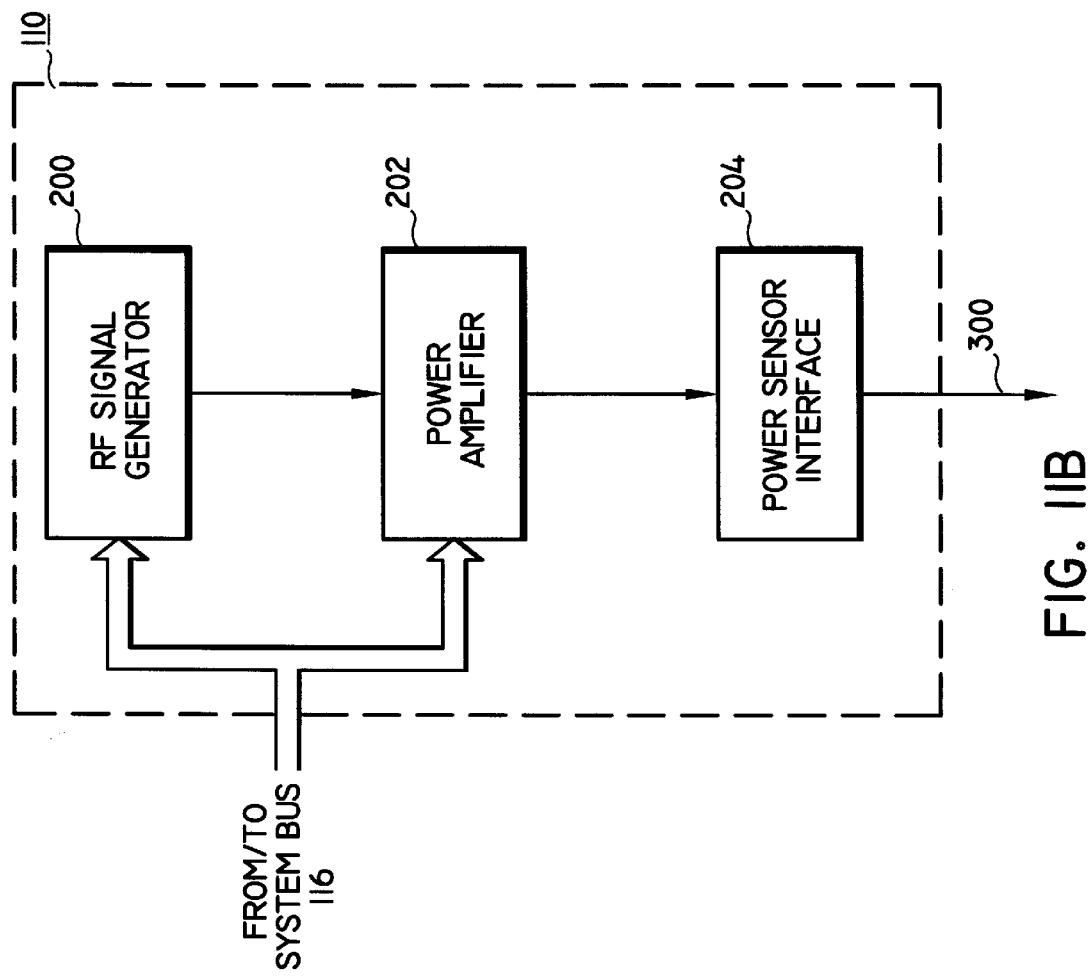
FIG. 11B is a block diagram illustrating the components of the power signal generator of the control system.
Figure 11A:
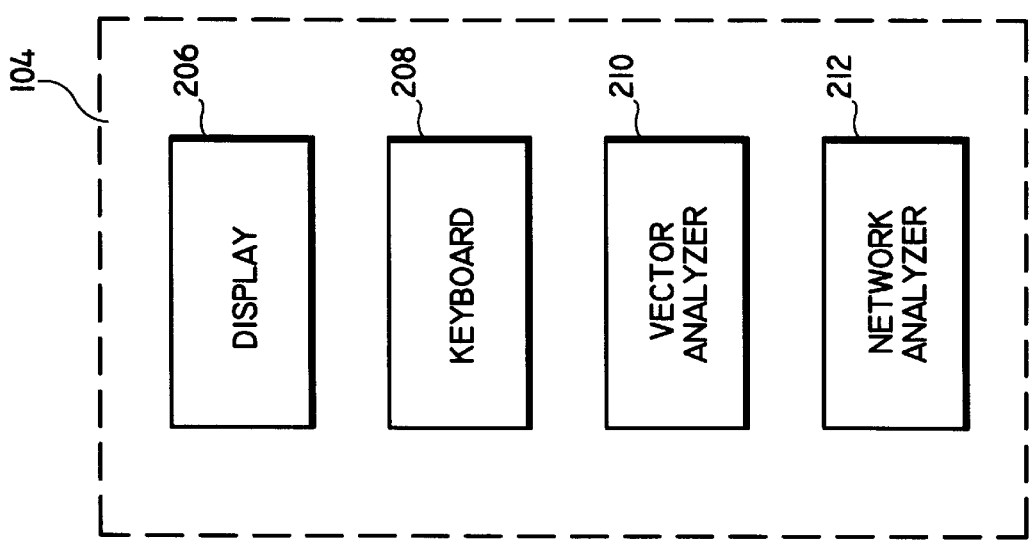
FIG. 11A is a block diagram illustrating the components of the input/output device of the control system of the TLEA system depicted in FIG. 1.

As depicted in FIG. 11A, I/O 104 may include an alphanumeric keypad 208 for inputting information to microprocessor system 102 and display 206 for outputting information, for example. In addition, I/O 104 can include a vector analyzer 210 and/or a true network analyzer 212 for receiving information from applicator interface 114 and outputting real time impedance measurement information. This allows microprocessor system 102 to also monitor the impedance of the tissue in the area being treated.

As depicted in more detail in FIG. 11B, power signal generator 110 includes RF signal generator 200, power amplifier 202 and power sensor interface 204. RF signal generator 200 can consist of a voltage control oscillator (VCO) such as a VCO manufactured by Mini-Circuits Inc., Brooklyn, N.Y., for example. RF signal generator 200 is controlled by microprocessor system 102 via system bus 116. RF signal generator 200 generates radio frequency signals preferably from below 1 MHZ to about 40 MHZ, and more preferably at about 40.68 MHZ, or alternately at microwave frequencies, which are approved FCC frequency standards for industrial, scientific and medical applications. The output of RF signal generator 200 is adjustable in 3 dB steps from −10 to +10 dBM. The output can also be trimmed from 0 to 3 dB. To allow for safety considerations, the output of RF signal generator 200 can be switched off by computer control or by use of an interlock system, for example. The RF signal generated by RF signal generator 200 is input to power amplifier 202, which power amplifies the RF signal to approximately 20 watts. Power amplifier 202 consists of a linear class A amplifier having a +30 dB gain with overload protection. Power amplifier 202 may also include features such as thermal overhead protection and output power foldback upon a short at the load. For safety considerations, the output of power amplifier 202 can also be switched off by use of an interlock system or by computer control. Power sensor interface 204 can consist of a diode detector connected to one port of a directional coupler, for example. The DC output of the diode detector can be processed by an A/D converter to provide for leveling of the output of power amplifier 202. In addition, the detector's DC output can be used for analog leveling of the output of RF signal generator 200. The power amplified RF signal output from power signal generator 110 is delivered to applicator interface 114, via cable 300. Cable 300 can consist of high quality Teflon coaxial cable such as RG-142 or RG-400, for example.

FIG. 11C, depicts in more detail the power signal generator/power amplifier subsystem including voltage control oscillator, adjustable attenuation module, power adjustment control, pre amplification module and power amplification module.

Figure 12:
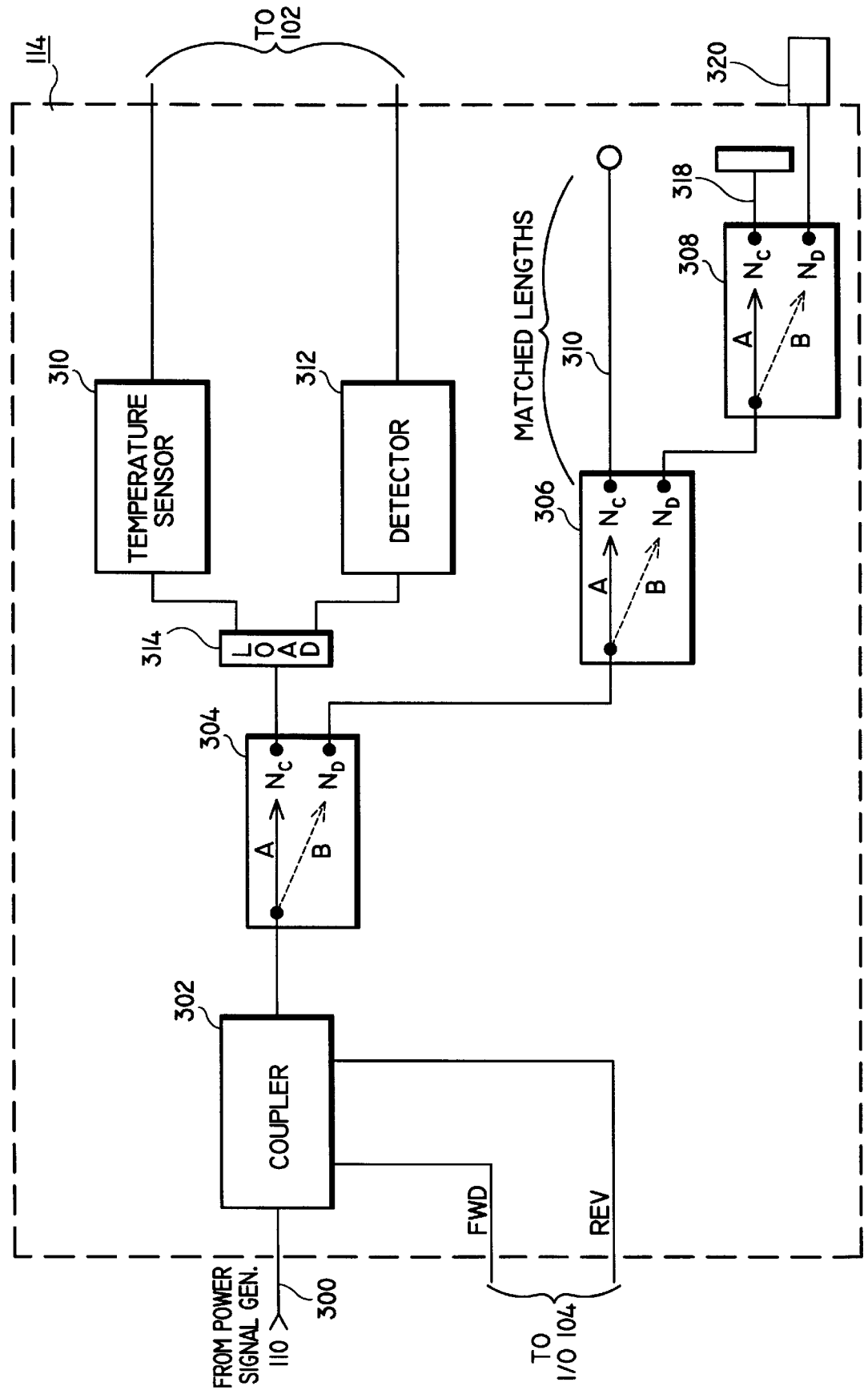
FIG. 12 is a block diagram illustrating the components of the applicator interface of the control system.

Applicator interface 114 is depicted in more detail in FIG. 12. Interface 114 provides for the calibrations necessary for accurate measurement of the prostate tissue impedance or dielectric properties. Preferably, interface 114 is located in close proximity (e.g., within 1 meter) to transurethral applicator 50 to insure measurement accuracy. Connected to input cable 300 is coupler 302. Coupler 302 is a dual port directional coupler having forward and reverse power coupled outputs. The coupled outputs of coupler 302 are provided to vector analyzer 210 and/or network analyzer 212. Vector analyzer 210 and/or network analyzer 212 process the information from the coupled outputs of coupler 302 and provide real time impedance measurement information to microprocessor system 102. Coaxial switch 304 can be manually controlled or, preferably, can be controlled by microprocessor system 102. When switch 304 is in position A, the output from power signal generator 110 is input to test load 314. Detector 312 consists of a diode detector that detects the output signal level at test load 314 and provides a corresponding signal to microprocessor system 102. Temperature sensor 310 monitors temperature at the test load and provides corresponding information to microprocessor system 102. When switch 304 is in position B, the output from signal generator 110 is provided to coaxial switch 306, which also can be manually or computer controlled. When switch 306 is in position A, the signal is provided to a predetermined length of coaxial cable 316, which terminates in an open. This open length of coaxial cable provides a reflected calibration signal to the network or vector analyzer. When switch 306 is in position B, the signal is provided to switch 308, which can also be controlled manually or by computer. When switch 308 is in position A, the signal is provided to a predetermined length of coaxial cable 318, which terminates in a short, thus providing another reflect calibration signal. Coaxial cables 316 and 318 should provide for matched electrical lengths to ensure calibration accuracy. When switch 308 is in position B, the signal is provided to output connector 320, which connects to the balun connected to the ablation electrodes. Accordingly, the entire electrical path from the directional coupler 302 to the balun input is calibrated to realize accurate impedance measurements of treatment tissue during the subsequent treatment.

Figure 13:
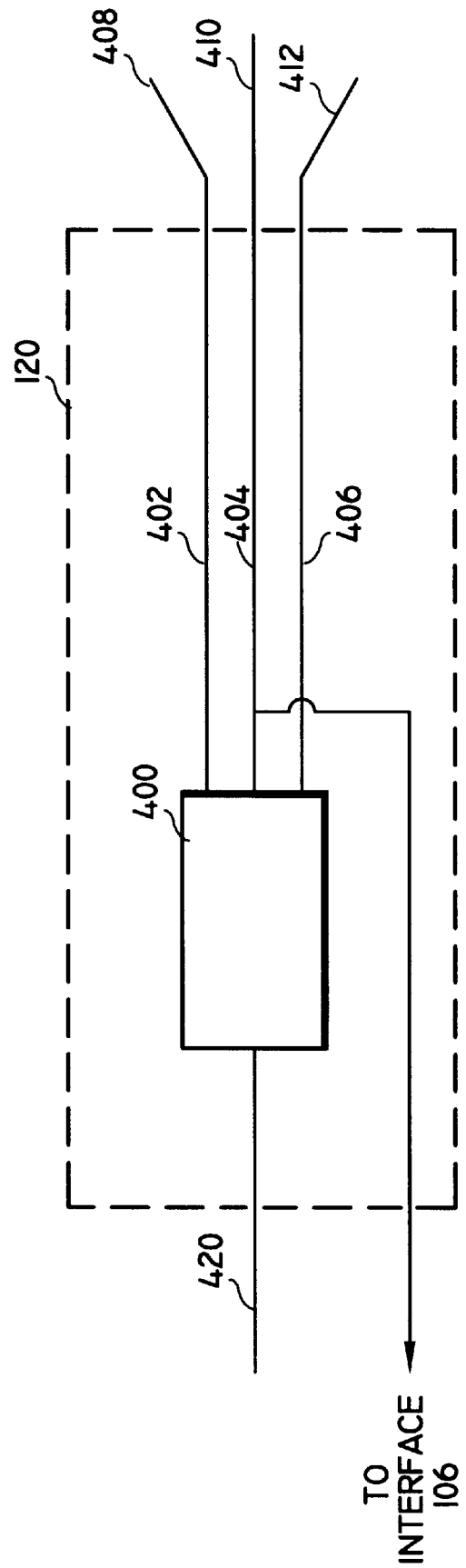
FIG. 13 is a block diagram illustrating the circuitry of the transurethral applicator.

As depicted in block diagram form in FIG. 13, transurethral applicator 50 includes balun 400 and three coaxial lines 402, 404 and 406 forming the three electrodes 72a, 72b and 72c, respectively. Balun 400 provides an interconnect between the coaxial transmission line 420 providing the RF power amplified signal from applicator interface 114, and the unbalanced coaxial transmission lines forming electrodes 72a, 72b and 72c. Balun 400 ensures that the currents flowing in electrodes 72a, 72b and 72c are equal and opposite and that the voltages to ground of each of the electrodes are equal and opposite, thus ensuring no radiation leakage in the unbalanced coaxial transmission lines. Balun 400 acts as an impedance transformer between coaxial cable 420 and the electrodes, thus ensuring maximum power transfer efficiency and therefore less power required for a given tissue temperature requirement.

The electrodes 72a, 72b and 72c may be provided with a tapered lossy dielectric coating or stepped lossy dielectric coating in the manner of a voltage divider network using different value resistors to achieve proper network current action. Each electrode 72a, 72b and 72c consists of an insulated wire inside an ungrounded coaxial metal tube (e.g., coaxial cables 402, 404 and 406). At stated above, at least one of the electrodes (preferably, center electrode 72c) includes a temperature sensing element. As noted previously, the temperature sensing element provides a signal to temperature sensor interface 106, which processes the signal and provides real time temperature information to microprocessor system 102.

In addition to providing temperature and impedance sensors, the present disclosure also contemplates the use of miniature external antenna sensors. Such sensors can be used to continually monitor the RF energy coupling into the tissue undergoing treatment, to insure safe and efficient energy application.

The combination of impedance and temperature measurements can be used to provide precise control of the BPH treatment. For example, the electrical impedance of the electrodes is a function of the volume of tissue between the electrodes, the tissue's dielectric properties and thermal conduction effects. That is, the electrical conductivity of the tissue being treated varies depending on the mobilization and removal of liquids from the heated volume of tissue and tissue volume changes. The impedance measured during heat application, thus provides a direct measurement of the dielectric properties of the tissue undergoing thermal treatment. Accordingly, during heat application treatment by the electrodes, the impedance of the treated tissue varies in a very specific manner that can be measured and analyzed.

Microprocessor system 102 thus uses the temperature measurements and the impedance measurements during treatment, to provide precise real time control of the physical process during treatment. This allows for the most effective application of RF energy for the intended BPH application to be provided.

It is also contemplated that the system measure phase angle and amplitude of the reflected power to measure complex impedance which in turn enables measurement of dielectric properties and conductivity of the tissue.

Although described herein as a bipolar RF electrode, it is also contemplated that the needles could be in the form of microwave antennas, coupled to each other in a phased array for higher frequency applications to speed up the time required to ablate the tissue. Insulation can be provided along the entire length of the probe.

Operation

Figure 14:
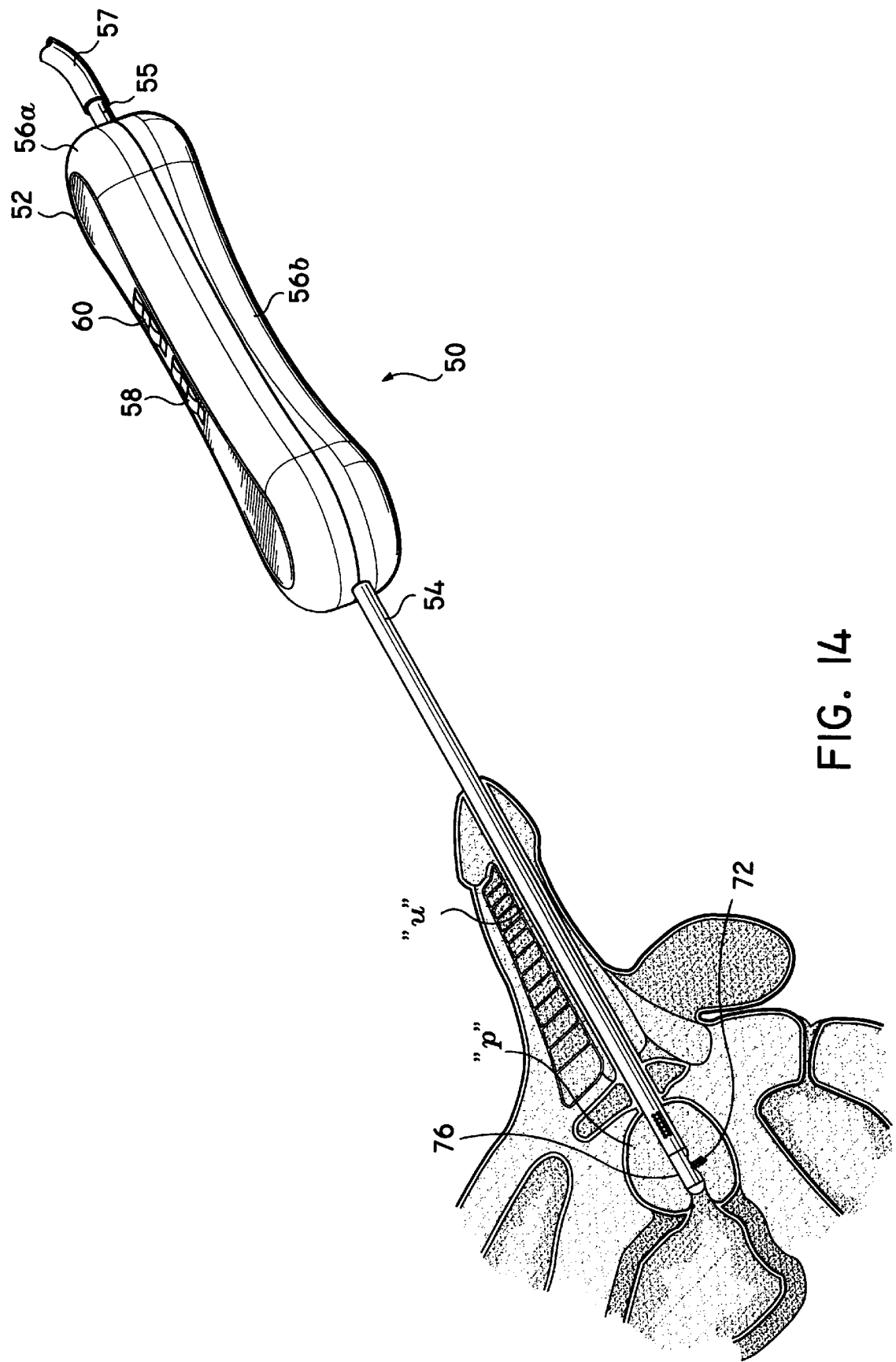
FIG. 14 is a view illustrating insertion of the transurethral applicator within the urethral passage of the patient with the electrodes in the deployed position penetrating the prostatic tissue.

Referring now to FIG. 14, applicator 50 is illustrated in conjunction with the thermal treatment of the prostate to alleviate the symptoms of BPH (hyperplasia). Applicator 50 in its non-activated condition is inserted through the urethral passage "u" and advanced until deployment tip 76 is adjacent the prostate gland "p". Actuating members 58, 60 are selectively proximally moved to deploy the electrodes 72a–72c whereby upon deployment the penetrating end portions 74a–74c of the electrodes pierce the urethral wall and enter into the prostate tissue. In the preferred embodiment, the deployed portions of the electrodes lie generally within the same plane as previously discussed. With the electrodes in the desired arrangement, the system is energized to thermally treat (e.g., ablate, vaporize or cauterize) the desired prostatic tissue with RF energy. As a result of this treatment, the prostatic tissue dies and necroses and possibly vaporizes, depending on frequency, thus, relieving pressure off of the urethral wall and alleviating the symptoms of BPH. During the treatment, the impedance and temperature measurements may be ascertained as stated above to monitor the functioning of the TLEA system and the state of the treated tissue.

The energy is applied to the tissue at a predetermined frequency varying by way of example between about 13 MHZ and about 40 MHZ. However, in an alternate embodiment, multiple frequency applications are utilized to obtain different tissue effects. For example, a lower frequency application of less than 1 MHZ can initially be used followed by a high frequency application of between approximately 13 MHZ and 40 MHZ to ablate the tissue.

During treatment of the prostatic tissue, the multiple electrodes may be deployed at varying lengths or depths in the prostate to selectively control the dimension of the thermal pattern generated by the electrodes. In particular, the length of the deployed portions of the electrode may be selectively adjusted in the prostatic tissue for a predetermined angular orientation of the side electrodes relative to the central electrode to permit specific regions to be targeted for thermal treatment thus providing heating pattern flexibility and control.

Figure 17:
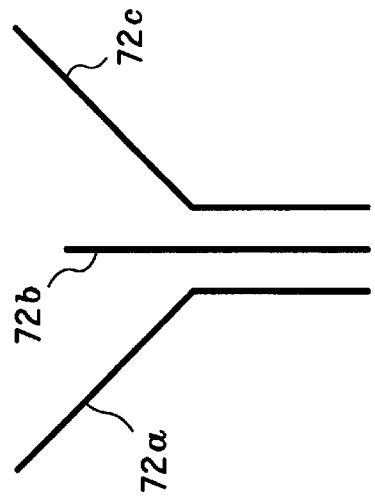
FIGS. 15–17 are examples of preferred arrangements of the three electrodes to produce desired heating patterns.
Figure 16:
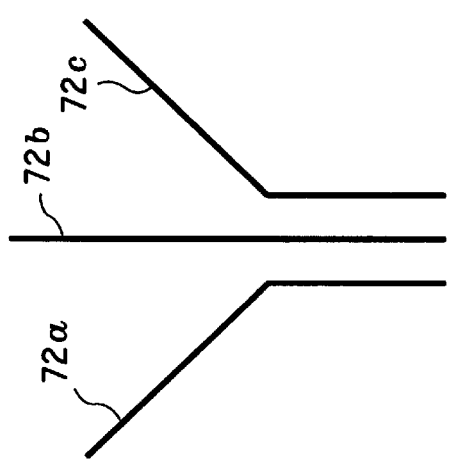
Figure 15:
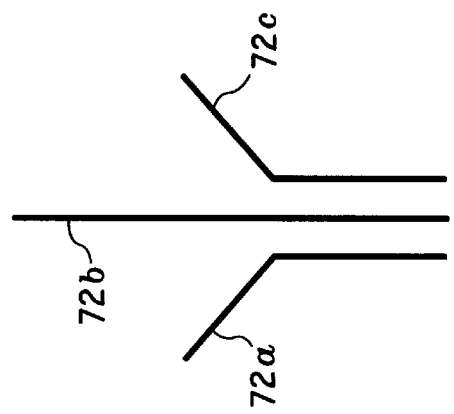

FIGS. 15–17 schematically depict three preferred configurations of the electrode arrangement. FIG. 15 depicts a specific electrode geometry where the lengths of the deployed energy radiating portions of the electrodes are represented by 1:2:1, i.e., the deployed portion of the center electrode 72c is about twice the length of the deployed portions of the side electrodes 72a and 72b. In one preferred embodiment, the exposed portions of the side electrodes 72a and 72b are about 1 cm in length while the exposed portions of the center electrode 72c is about 2 cm in length. This particular arrangement (1:2:1) provides a rounded heating pattern at the end of the electrode array. FIG. 16 depicts an arrangement represented as 2:2:2, i.e. the deployed length of all three electrodes is substantially equal (e.g., each exposed portion of the electrode is about 2 cm long). This particular arrangement (2:2:2) defines a wedge-shaped heating pattern. FIG. 17 depicts an electrode arrangement represented by (2:1:2) wherein the deployed portion of the side electrodes is twice the length of the deployed portion of the center electrode, e.g. about 2 cm and about 1 cm, respectively. This provides a tulip shaped pattern. For each embodiment, the deployed electrode portions of electrodes 72a–72c lie within the same plane and the angles defined between the center electrode 72c and the side electrodes 72a and 72b are equal to provide a symmetrical heating pattern. It is to be appreciated that the angular arrangement of the deployed electrode portions may be varied as well to provide alternate heating pattern configurations.

Figure 18:
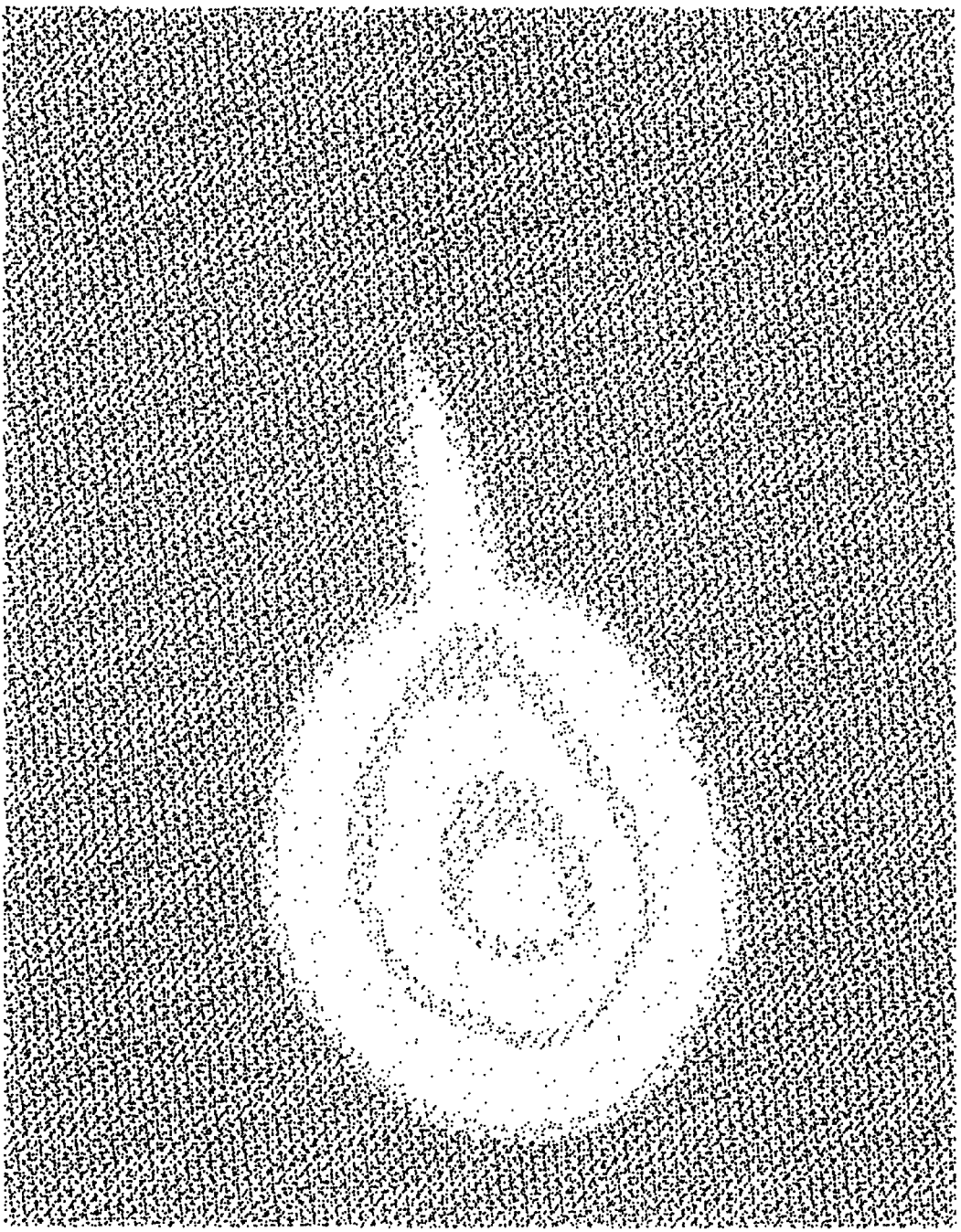
FIGS. 18–20 are computer generated images of thermal patterns created within tissue with the TLEA electrode arrangements of FIGS. 15–17.
Figure 19:
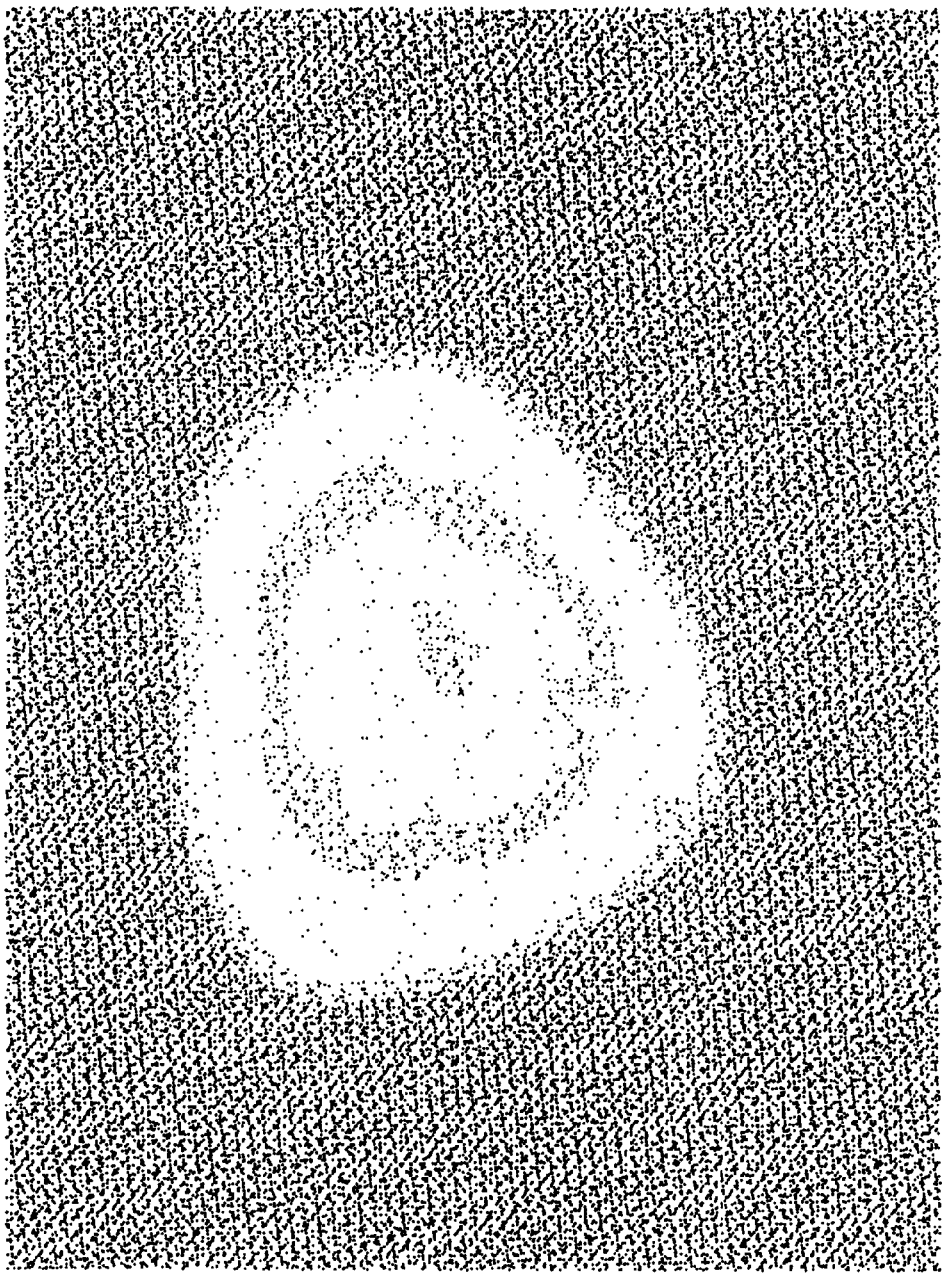
Figure 20:
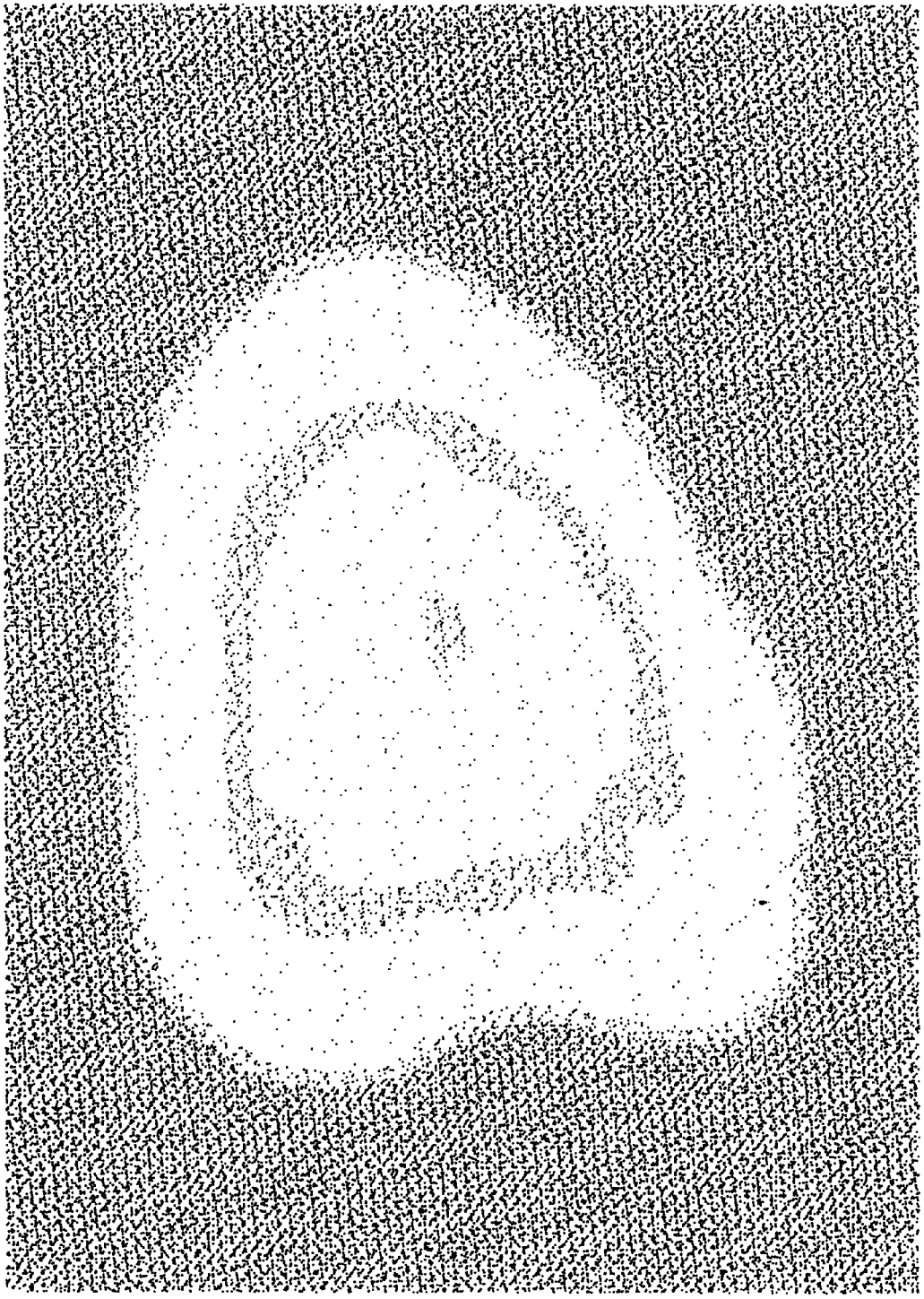

FIGS. 18–20 are a computer generated images of thermal patterns created within tissue with aforementioned electrode arrangements of FIGS. 15–17. FIG. 18 illustrates the generally circular heating pattern effected by the arrangement of FIG. 15 while FIG. 19 illustrates the wedge-shaped heating pattern effected by the electrode arrangement of FIG. 16. FIG. 20 details the tulip-shaped thermal heating pattern created by the electrode arrangement of FIG. 17.

A While the disclosure has been particularly shown and described with reference to the preferred embodiments, it will be understood by those skilled in the art that various modifications and changes in form and detail may be made therein without departing from the scope and spirit. Accordingly, modifications such as those suggested above, but not limited thereto, are to be considered within the scope.

What is claimed is:

1. A system for the radiofrequency hyperthermia treatment of prostatic tissue, which comprises:
   a transurethral applicator including:
      a housing;
      an elongated portion extending from the housing and dimensioned to be introduced within the urethral passage of a patient;
      at least three radiofrequency bipolar electrodes supported within the elongated portion and being deployable to penetrate a urethra wall defining the urethral passage and enter prostatic tissue to define a predetermined electrode arrangement therein;
      a deployment mechanism associated with the housing for deploying the at least three bipolar electrodes, the deployment mechanism including a first actuator connected to a first bipolar electrode and selectively movable to selectively deploy the first bipolar electrode and a second actuator connected to a second and a third bipolar electrode and selectively movable to selectively deploy the second and the third bipolar electrodes to control positioning of the second and third bipolar electrode relative to the first bipolar electrode; and a radiofrequency source connected to the three bipolar electrodes for supplying radiofrequency energy such that the predetermined electrode arrangement generates a three dimensional thermal energy pattern within the prostatic tissue.

2. The system according to claim 1 wherein the deployment mechanism is adapted to deploy the bipolar electrodes to define a predetermined electrode arrangement wherein the second and third bipolar electrodes are symmetrically arranged about the first bipolar electrode.

3. The system according to claim 2, wherein the elongated portion of the applicator has a distal deployment tip portion associated therewith, the deployment tip portion defining deployment ports, configured and dimensioned to deploy the bipolar electrodes such that the first, second and third bipolar electrodes lie substantially within the same general plane.

4. The system of claim 1, further including means for initially supplying said radiofrequency (RF) energy at frequency of less than one MHZ and then supplying said RF energy at a frequency in the range of about 13–40 MHz to ablate target tissue.

5. The system of claim 1, wherein said electrodes are provided with a lossy dielectric coating to influence current flow on the electrodes.

6. The system according to claim 1 including a temperature sensor associated with a distal end portion of the elongated portion to monitor the temperature of the tissue adjacent the distal end portion.

7. The system of claim 1, further including a balun for transforming impedance between a coaxial cable that supplies RF energy from said RF source, and impedance measurement circuitry coupled to said coaxial cable for measuring impedance of treatment tissue.

8. The system according to claim 1, further including a control unit having a coaxial output providing RF energy to said electrodes, and a balun interconnecting said electrodes with said coaxial output, said control unit comprising:

a processor system that monitors impedance of tissue in the area being treated;

a directional coupler coupled between said radiofrequency source and said coaxial output for providing forward and reverse power to an interface that provides impedance information to said processor system;

at least one switch for switching the output of said directional coupler between a first electrical path terminating in a short circuit, a second electrical path terminating in a test load, and a third electrical path terminating in an open circuit, to enable an impedance calibration to be performed; and said at least one switch being further capable of switching said directional coupler output to a fourth electrical path including said coaxial output and said balun, to provide RF energy to said electrodes and to enable said directional coupler to couple reverse power during treatment towards said interface for calibrated impedance monitoring.

9. The system of claim 8, wherein said interface comprises a vector analyzer.

10. The system of claim 9, wherein said interface comprises a network analyzer.

11. The system of claim 8, further including a temperature sensor for monitoring temperature at the test load and providing corresponding information to said processor system.

12. The system of claim 8, wherein said radiofrequency source provides RF energy at a frequency of about 40 MHZ or less.

13. The system of claim 8, further comprising a detector for detecting an output signal level at said test load and providing corresponding information to said processor system.

14. An apparatus for treating prostatic tissue comprising:
a) a handle assembly;
b) an elongate body extending distally from the handle assembly and having an axial bore extending at least partially therethrough defining a longitudinal axis;
c) first, second, and third elongated probes supported within the elongate body and mounted for movement between respective retracted positions disposed within the axial bore and respective deployed positions projecting outwardly from a distal end portion of the elongate body;
d) a first actuator associated with the handle assembly and operatively connected to the first probe for selectively moving the first probe between the retracted and deployed positions thereof independent of the second and third probes;
e) a second actuator associated with the handle assembly and operatively connected to the second and third probes for selectively and conjunctively moving the second and third probes between the retracted and deployed positions thereof independent of the first probe; and
f) means for operatively connecting the first, second and third probes to an external source of radiofrequency energy.

15. An apparatus as recited in claim 14, wherein first, second and third guide channels are defined in a distal end portion of the elongated body in communication with the axial bore thereof for respectively directing the first second and third probes outwardly toward the respective deployed positions thereof.

16. An apparatus as recited in claim 14, wherein the first, second and third probes are each configured as a bipolar electrode.

17. An apparatus as recited in claim 16, wherein each probe defines a distal radiating segment and wherein upon deployment of the first, second and third probes the distal radiating segments are oriented within the same geometric plane.

18. A method for the hyperthermia treatment of prostatic tissue, comprising the steps of:

inserting a transurethral applicator within the urethral passage of a patient, the applicator including at least first, second and third radiofrequency bipolar electrodes supported therein;

deploying the bipolar electrodes from the applicator whereby the bipolar electrodes penetrate the urethral wall and enter prostatic tissue to define a predetermined electrode arrangement of the bipolar electrodes within the prostatic tissue, the second and third bipolar electrodes being deployed independent of the first bipolar electrode;

supplying radiofrequency energy to the electrode arrangement whereby the electrode arrangement generates a three dimensional thermal energy pattern within the prostatic tissue.

19. the method according to claim 18, wherein the step of deploying includes deploying the three bipolar electrodes from the applicator to define a predetermined electrode arrangement characterized by having a first centrally disposed bipolar electrode and second and third bipolar electrodes symmetrically arranged about the first centrally disposed bipolar electrode.

20. The method according to claim 19, wherein the step of deploying includes deploying the three bipolar electrodes such that the first, second and third bipolar electrodes generally lie within the same place.

21. The method according to claim 20, wherein the step of deploying includes deploying the three bipolar electrodes such that the second and third bipolar electrodes define an angle ranging from about 5° to 85° relative to the first bipolar electrode.

* * * * *